(12) United States Patent
Sato (10) Patent No.: US 8,815,153 B2
(45) Date of Patent: Aug. 26, 2014

(54) AUTOMATIC ANALYZER AND REAGENT STORAGE THEREOF

(75) Inventor: Naoto Sato, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1438 days.

(21) Appl. No.: 12/146,884

(22) Filed: Jun. 26, 2008

(65) Prior Publication Data

US 2009/0004057 A1  Jan. 1, 2009

(30) Foreign Application Priority Data

Jun. 29, 2007  (JP) ................................. 2007-172252

(51) Int. Cl.
   *G01N 21/00*   (2006.01)
(52) U.S. Cl.
   USPC ............... 422/63; 422/50; 422/500; 422/501; 422/502; 422/62; 422/64; 422/65; 422/66; 422/67; 436/180

(58) Field of Classification Search
   USPC ................. 422/500–502, 62–67, 50; 436/180
   See application file for complete search history.

(56) References Cited

FOREIGN PATENT DOCUMENTS

JP   2005-283529   10/2005

*Primary Examiner* — Jyoti Nagpaul
(74) *Attorney, Agent, or Firm* — Oblon, Spivak, McClelland, Maier & Neustadt, L.L.P.

(57) ABSTRACT

A holding unit pivotally holds a plurality of reagent bottles which store reagents. A reagent case houses the holding unit and has an edge higher than at least the housed holding unit. The reagent cover is a cover for closing the reagent case. A cooling unit is mounted on one outer surface of the reagent case and cools air in the reagent case closed by the reagent cover through one outer surface. A circulating unit is mounted on the holding portion and circulates the cooled air in the reagent case closed by the reagent cover.

24 Claims, 8 Drawing Sheets

AUTOMATIC ANALYZER AND REAGENT STORAGE THEREOF

CROSS-REFERENCE TO RELATED APPLICATIONS

This application is based upon and claims the benefit of priority from prior Japanese Patent Application No. 2007-172252, filed Jun. 29, 2007, the entire contents of which are incorporated herein by reference.

BACKGROUND OF THE INVENTION

1. Field of the Invention

The present invention relates to an automatic analyzer which analyzes the components of a test sample extracted from a test object and a reagent storage of the analyzer and, more particularly, to an automatic analyzer and its reagent storage which can store and cool reagents.

2. Description of the Related Art

An automatic analyzer is targeted for biochemical test items, immunological test items, and the like. The automatic analyzer obtains the concentrations of various components and the activities of enzymes in test samples by measuring changes in color tone and the like which are caused by reactions of mixtures of the test samples dispensed into reaction vessels and reagents corresponding to the respective items. This automatic analyzer performs measurement of an item selected in accordance with a test from many items made measurable upon setting of analytical conditions for each test sample. The test sample and a reagent corresponding to the selected item are dispensed into a reaction vessel with a sample probe and a reagent dispensing probe, and the mixture of the dispensed test sample and reagent is stirred by a stirrer. A photometric unit then performs measurement of the mixture.

Reagent bottles equal in number to measurable items are stored in a reagent case in a reagent storage and a reagent cover which covers the reagent case. The stored reagent bottles are kept cool to prevent analytical data from deteriorating upon degeneration of the reagents. As a method of keeping reagent bottles cool, there is available a method of cooling the reagent case and keeping the reagent bottles cool by natural diffusion of cool air in the reagent case. There is also known a keeping cool method which can make uniform a temperature distribution by sending cool air around the reagent bottles in the reagent case regardless of the arrangement of the reagent bottles in the reagent case (see, for example, Jpn. Pat. Appln. KOKAI Publication No. 2005-283529).

According to the method of keeping a reagent case cool, however, the temperature distribution of air in the reagent case is not uniform. This makes it impossible to keep the reagents in all the reagent bottles in the reagent case at a predetermined temperature. According to the method of sending cool air into the reagent case, if many reagent bottles are stored, since cool air is blown against only partial surfaces of the reagent bottles, it takes much time to lower the temperature of each bottle to a predetermined temperature. Furthermore, the reagent bottles are stored while the cover is open. As a consequence, evaporation increases the reagent concentrations to deteriorate analytical data.

BRIEF SUMMARY OF THE INVENTION

The present invention has been made to solve the above problems, and has as its object to provide an automatic analyzer and its reagent storage which can efficiently keep the reagents cool in reagent bottles.

According to a first aspect of the present invention, there is provided a reagent storage for an automatic analyzer comprising: a holding unit which pivotally holds a plurality of reagent bottles which store reagents; a case which houses the holding unit and has an edge higher than at least the housed holding unit; a cover for the closing case; a cooling unit which is mounted on one outer surface of the case and cools air in the case closed by the cover through said one outer surface; and a circulating unit which is mounted on the holding unit and circulates the cooled air in the case closed by the cover.

According to a second aspect of the present invention, there is provided a reagent storage of an automatic analyzer comprising: a case which houses a reagent bottle storing a reagent; a cover for closing the case; a holding unit which is arranged in the case closed by the cover so as to be spaced apart from the case and the cover and hold the reagent bottles which are spaced apart from each other by a predetermined interval; and a circulating unit which connects a first space between an inner bottom surface of the case and a bottom portion of the holding unit to a second space formed between adjacent reagent bottles held by the holding unit, connects the second space to a third space formed near a center of the holding unit, aspirates air from the third space, and discharges air cooled in the first space into the second space.

According to a third aspect of the present invention, there is provided an automatic analyzer comprising: a reagent storage which stores a reagent; and a measurement unit which measures a mixture of the reagent and a sample, the reagent storage comprising: a holding unit which pivotally holds a plurality of reagent bottles which store reagents; a case which houses the holding unit and has an edge higher than at least the housed holding unit; a cover for closing the case; a cooling unit which is mounted on one outer surface of the case and cools air in the case closed by the cover through the one outer surface; and a circulating unit which is mounted on the holding unit and circulates the cooled air in the case closed by the cover.

According to a fourth aspect of the present invention, there is provided an automatic analyzer which dispenses a sample and a reagent and measures a mixture thereof, the apparatus comprising a reagent storage having a case which houses a reagent bottle storing the reagent and a cover which covers the case, and the reagent storage comprising: a holding unit which is arranged in the case closed by the cover so as to be spaced apart from the case and the cover and hold the reagent bottles which are spaced apart from each other by a predetermined interval; a cooling unit which cools the case; and a circulating unit which connects a first space between an inner bottom surface of the case and a bottom portion of the holding portion to a second space formed between adjacent reagent bottles held by the holding unit, connects the second space to a third space formed near a center of the holding unit, aspirates air from the third space, and discharges air cooled in the first space into the second space.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An automatic analyzer according to an embodiment of the present invention will be described below with reference to FIGS. 1 to 9.

Figure 1:
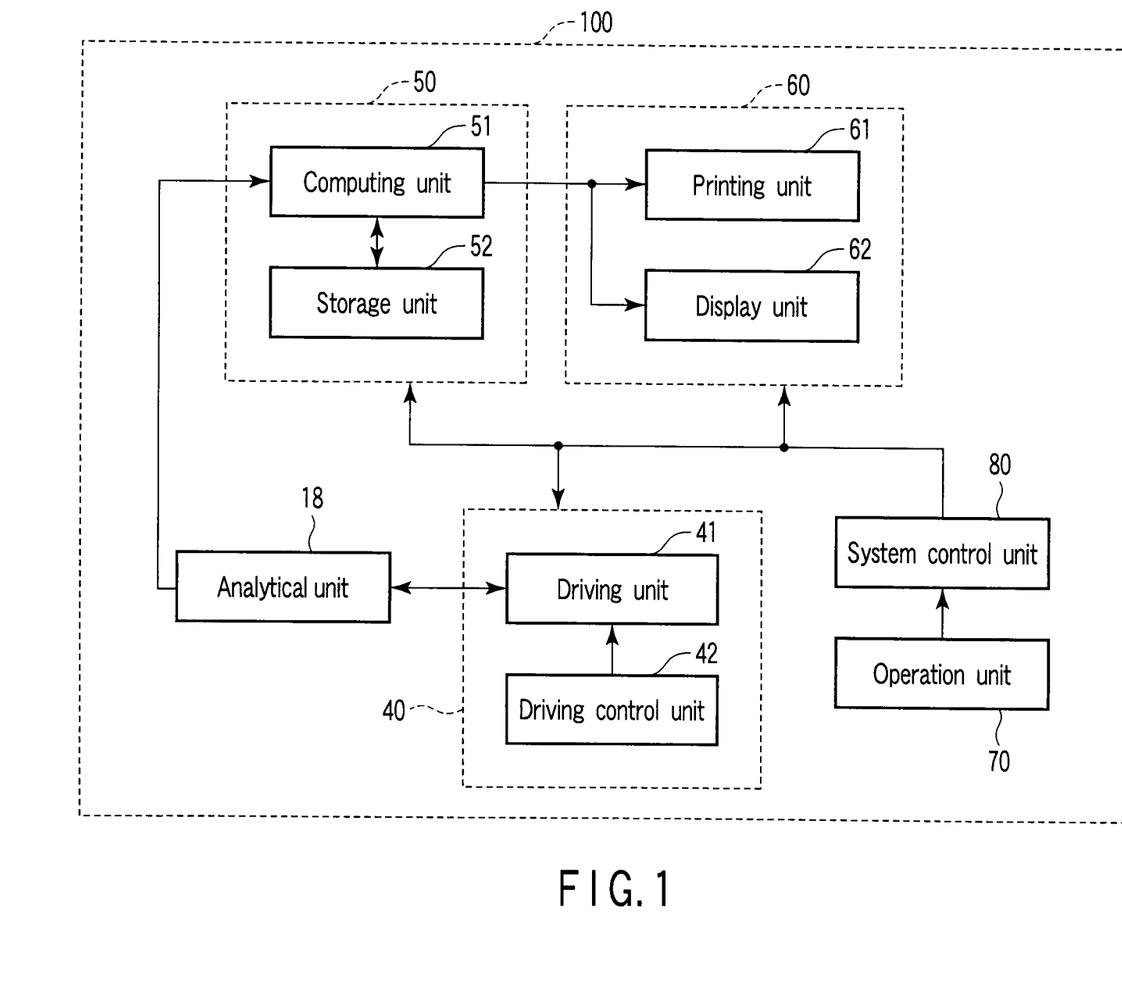
FIG. 1 is a block diagram showing the arrangement of an automatic analyzer according to an embodiment of the present invention.

FIG. 1 is a block diagram showing the arrangement of an automatic analyzer 100 according to an embodiment of the present invention. The automatic analyzer 100 includes an analytical unit 18, an analytical control unit 40, a data processing unit 50, an output unit 60, an operation unit 70, and a system control unit 80. The analytical unit 18 measures standard samples and test samples corresponding to various items on an item basis. The analytical control unit 40 controls the measuring operation of the analytical unit 18. The data processing unit 50 generates a calibration curve and analytical data by processing the standard sample data and test sample data output from the analytical unit 18. The output unit 60 outputs the calibration curve and analytical data generated by the data processing unit 50. The operation unit 70 inputs analytical conditions associated with a standard sample corresponding to each item and a calibration curve, various command signals, and the like. The system control unit 80 systematically controls the analytical control unit 40, data processing unit 50, and output unit 60.

Figure 2:
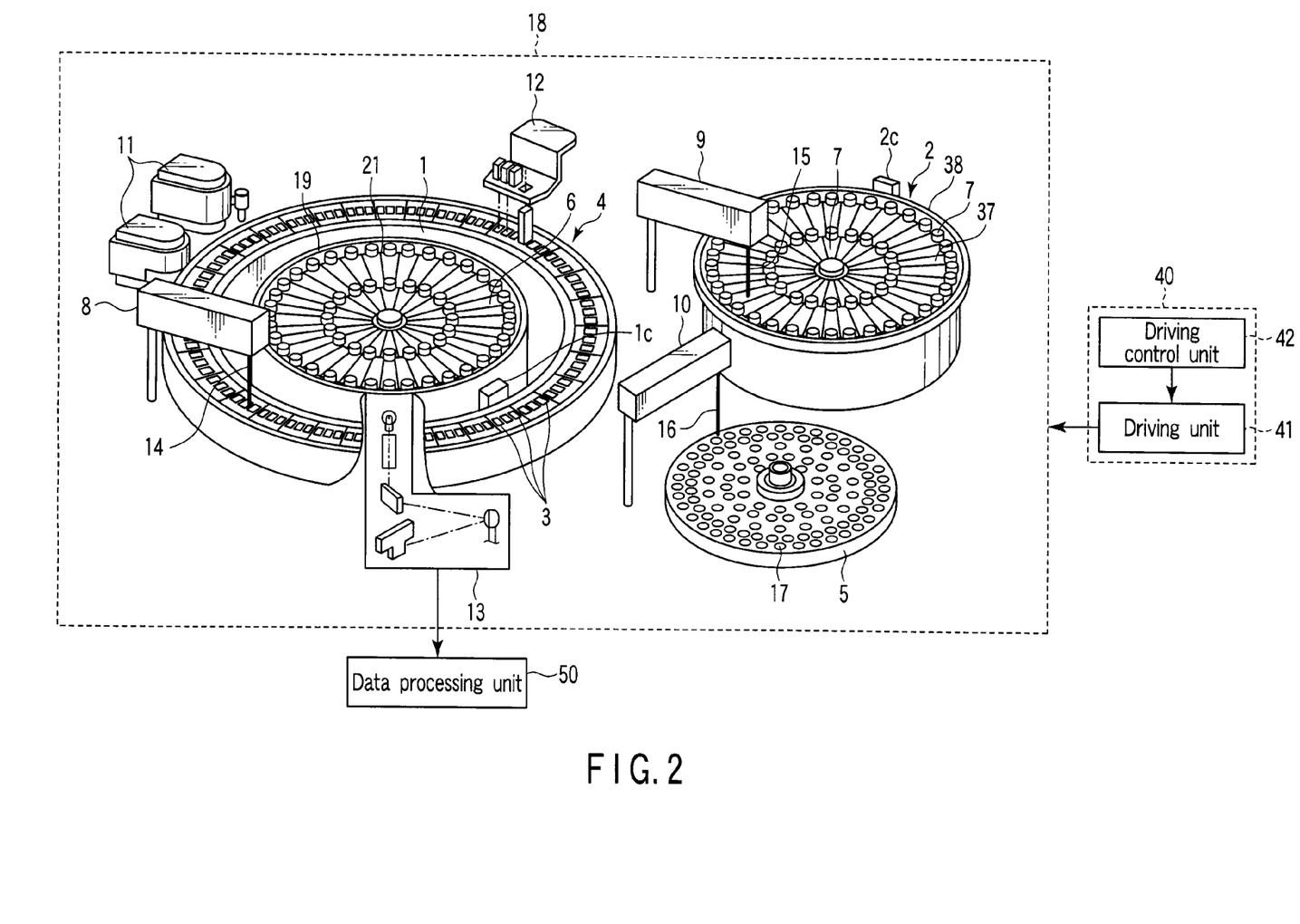
FIG. 2 is a perspective view showing the arrangement of an analytical unit in FIG. 1.

FIG. 2 is a perspective view showing the arrangement of the analytical unit 18. The analytical unit 18 comprises sample bottles 17, a disk sampler 5, reagent bottles 6, and a first reagent storage 1. The sample bottles 17 store samples such as standard and test samples. The disk sampler 5 pivotally holds the sample bottles 17. The reagent bottle 6 stores the first reagent for analyzing a component which is contained in a sample and corresponds to each item. The first reagent storage 1 includes a holding unit 21 which pivotally holds the reagent bottles 6 and a reagent case unit 19 which houses the holding unit 21.

The analytical unit 18 comprises a reader 1c, reagent bottles 7, a second reagent storage 2, and a reader 2c. The reader 1c reads the information of a bar code label attached to the reagent bottle 6. The reagent bottle 7 stores the second reagent paired with the first reagent. The second reagent storage 2 includes a holding unit 37 which pivotally holds the reagent bottles 7 and a reagent case unit 38 in which the holding unit 37 is housed. The reader 2c reads the information of a bar code label attached to the reagent bottle 7.

The analytical unit 18 comprises a sample dispensing probe 16, a first reagent dispensing probe 14, a second reagent dispensing probe 15, a sample dispensing arm 10, a first reagent dispensing arm 8, and a second reagent dispensing arm 9. The sample dispensing probe 16 aspirates a sample from the sample bottle 17 and discharges it into a reaction vessel 3. The first reagent dispensing probe 14 aspirates the first reagent from the first reagent bottle 6 in the first reagent storage 1 and discharges it into the reaction vessel 3. The second reagent dispensing probe 15 aspirates the second reagent from the second reagent bottle 7 in the second reagent storage 2 and discharges it into the reaction vessel 3. The sample dispensing arm 10 holds the sample dispensing probe 16 so as to allow it to pivot and move vertically. The first reagent dispensing arm 8 holds the first reagent dispensing probe 14 so as to allow it to pivot and move vertically. The second reagent dispensing arm 9 holds the second reagent dispensing probe 15 so as to allow it to pivot and move vertically.

The analytical unit 18 comprises a reaction disk 4, a stirring unit 11, a photometric unit 13, and a cleaning unit 12. The reaction disk 4 pivotally and movably holds the plurality of reaction vessels 3 arranged on the circumference. The reaction vessels 3 contain the samples, first reagents, and second reagents discharged from the respective dispensing probes. The stirring unit 11 stirs the mixture of the sample and first reagent dispensed into the reaction vessel 3 or the mixture of the sample and first and second reagents dispensed into the reaction vessel 3. The photometric unit 13 applies light to the reaction vessel 3 which rotates and moves. And the photometric unit 13 converts light transmitted through a liquid mixture containing a standard sample into an absorbance, thereby generating standard sample data. The photometric unit 13 then outputs the generated standard sample data to the data processing unit 50. The photometric unit 13 also generates test sample data by converting light transmitted through a liquid mixture containing a test sample into an absorbance. The photometric unit 13 then outputs the generated test sample data to the data processing unit 50. The cleaning unit 12 holds a cleaning nozzle and a drying nozzle so as to allow them to move vertically. The cleaning nozzle aspirates the liquid mixture in each reaction vessel 3 which has undergone measurement and cleans the inside of the reaction vessel 3. The drying nozzle dries the interior of the reaction vessel 3. The reaction vessel 3, sample dispensing probe 16, first reagent dispensing probe 14, second reagent dispensing probe 15, stirring unit 11, and the like after measurement are cleaned and used for measurement again.

The analytical control unit 40 comprises a drive unit 41 and a drive control unit 42. The drive unit 41 drives the respective devices by supplying drive signals to the respective mechanisms of the analytical unit 18. The drive control unit 42 supplies a control signal to the drive unit 41 to make it supply a drive signal corresponding to the control signal. More specifically, the drive unit 41 pivots the holding unit 21 of the first reagent storage 1, the holding portion 37 of the second reagent storage 2, and the disk sampler 5. The drive unit 41 rotates the reaction disk 4. The drive unit 41 pivots and moves vertically the sample dispensing arm 10, first reagent dispensing arm 8, second reagent dispensing arm 9, and stirring unit 11. The drive unit 41 moves the cleaning unit 12 vertically.

The drive unit 41 drives a sample dispensing pump to make the sample dispensing probe 16 aspirate and discharge a sample. The drive unit 41 drives a first reagent pump to make the first reagent dispensing probe 14 aspirate and discharge the first reagent. The drive unit 41 drives the second reagent pump to make the second reagent dispensing probe 15 aspirate and discharge the second reagent. The drive unit 41 drives the stirrer of the stirring unit 11 to make it stir. The drive unit 41 drives a cleaning pump to make the cleaning nozzle of the cleaning unit 12 aspirate a liquid mixture or discharge and aspirate a cleaning liquid. The drive unit 41 drives a drying pump to make the drying nozzle of the cleaning unit 12 dry.

The data processing unit 50 comprises a computing unit 51 and a storage unit 52. The computing unit 51 generates a calibration curve from standard sample data corresponding to each item which is output from the photometric unit 13 of the analytical unit 18. For test sample data corresponding to each item, the computing unit 51 reads out a calibration curve corresponding to the item from the storage unit 52, and generates analytical data about a concentration, activity value, and the like by using the readout calibration curve.

The storage unit 52 comprises a hard disk and the like. The storage unit 52 stores the calibration curves output from the computing unit 51 for each item. The storage unit 52 also stores the analytical data output from the computing unit 51 for each test sample.

The output unit 60 comprises a printing unit 61 and a display unit 62. The printing unit 61 includes a printer and the like. The display unit 62 prints calibration curves, analytical data, and the like on printer sheets on the basis of a predetermined format. The display unit 62 comprises a monitor such as a CRT or a liquid crystal panel. The display unit 62 displays the calibration curves and analytical data output from the data processing unit 50. The display unit 62 displays a window for setting analytical conditions for each item, e.g., a reagent amount, a wavelength, and a sample amount, a window for inputting test object information, e.g., a test object ID and a test object name, a window for selecting items to be measured for each test sample, and the like.

The operation unit 70 comprises input devices such as a keyboard, a mouse, buttons, and a touch key panel (which are not shown). The operation unit 70 inputs analytical conditions for each item, test object information such as the test object ID of a test object and a test object name, measurement items for each test sample, and the like.

The system control unit 80 comprises a CPU (which are not shown) and a storage circuit (which are not shown). The system control unit 80 stores information such as the command signals supplied from the operation unit 70, analytical conditions for each item, test object information, and measurement items for each test object. The system control unit 80 causes the respective mechanisms of the analytical unit 18 to operate under a predetermined operation condition in a predetermined analytical cycle and controls the overall system on the basis of these pieces of information.

Figure 3:
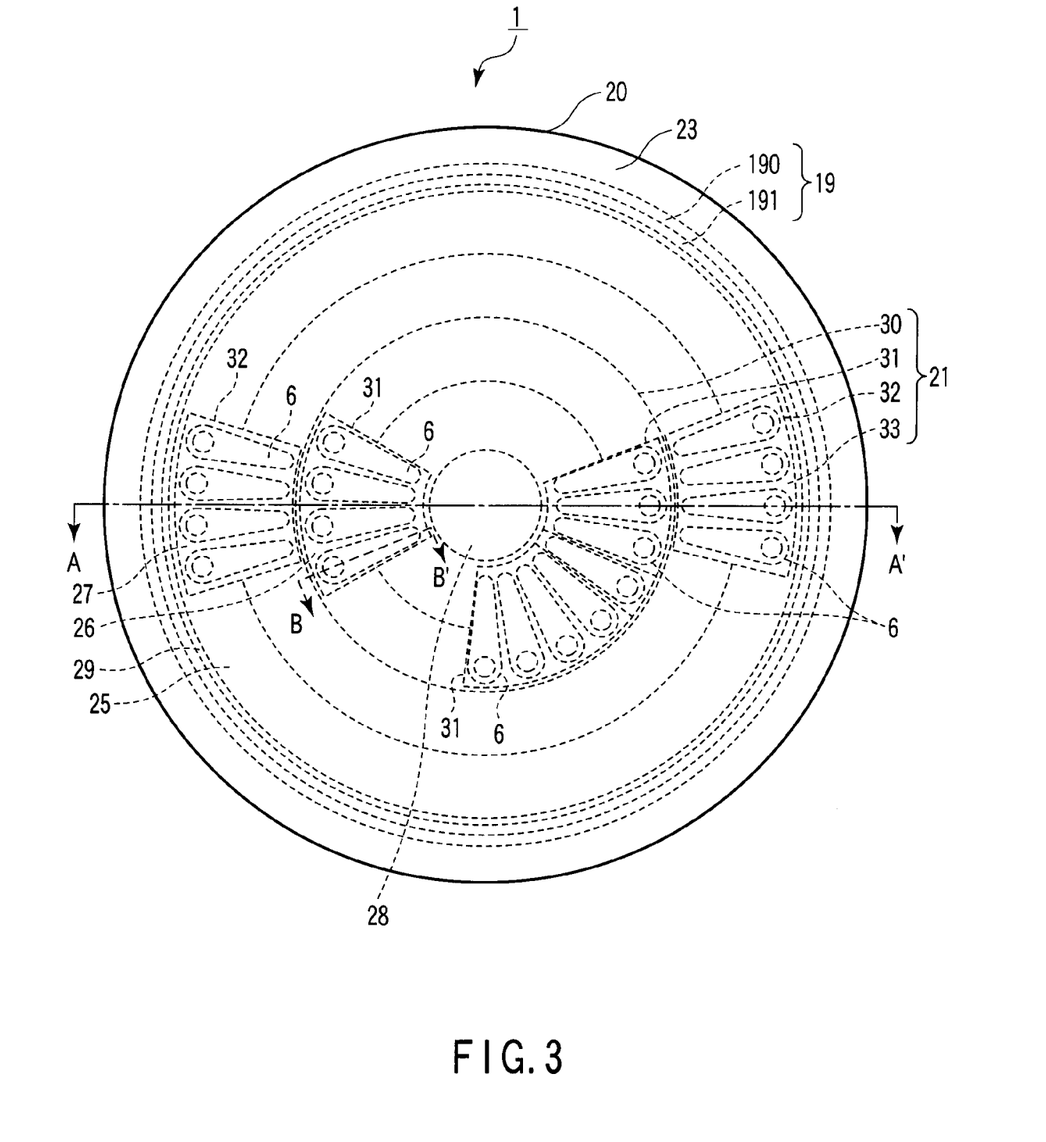
FIG. 3 is a view showing the first reagent storage in FIG. 2 when viewed from above.
Figure 4:
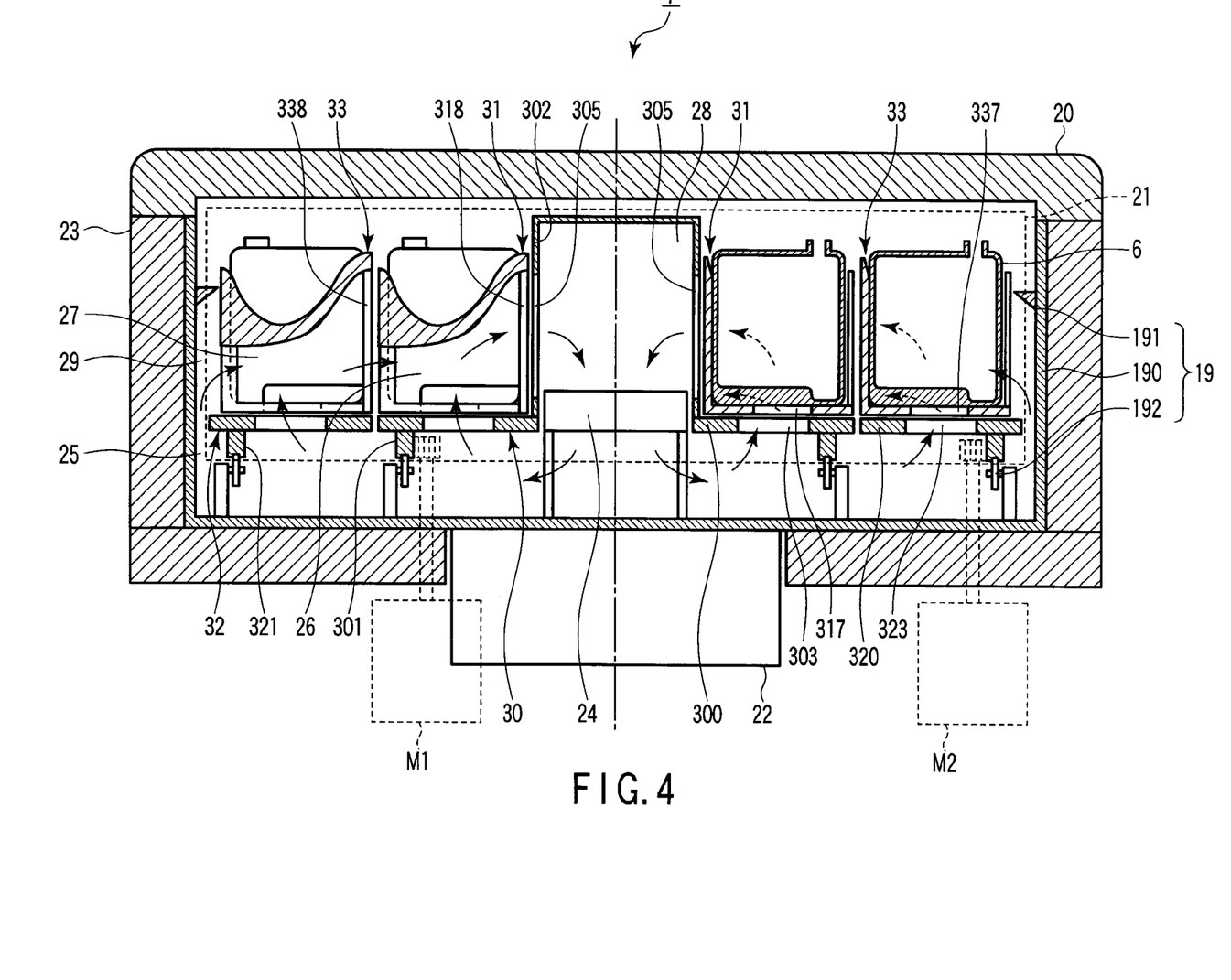
FIG. 4 is a sectional view of the first reagent storage taken along line A-A' of FIG. 3.

The arrangements of the first and second reagent storages 1 and 2 will be described next with reference to FIGS. 3 and 4. FIG. 3 is a view showing the first reagent storage 1 when viewed from above. FIG. 4 is a sectional view of the first reagent storage 1 taken along line A-A' of FIG. 3.

As shown in FIGS. 3 and 4, the first reagent storage 1 comprises the reagent case unit 19, a reagent cover 20, the holding unit 21, a cooling unit 22, a thermal insulating unit 23, and a circulating unit 24.

The reagent case unit 19 houses the reagent bottles 6. The reagent case unit 19 comprises a reagent case 190, a projection 191, and a plurality of rollers 192. The reagent case 190 is made of a material with a high thermal conductivity such as aluminum. The reagent case 190 has a circular opening on the upper side. The reagent case 190 houses the holding unit 21 and has an edge higher than the housed holding unit 21. The projection 191 is mounted on the inner side surface of the reagent case 190 so as to surround the holding unit 21. The projection 191 protrudes from the inner side surface of the reagent case 190 to a side portion of the holding unit 21. The projection 191 is provided to prevent air in a fourth space 29 from flowing out to above the reagent bottles 6. The rollers 192 are attached to the inner bottom surface of the reagent case 190. The rollers 192 are engaged with the holding unit 21. The rollers 192 are rotatably arranged on the first circumference of the inner bottom surface of the reagent case 190 and the second circumference outside the first circumference. The rollers 192 support the holding unit 21 from below.

The reagent cover 20 is detachably attached to the reagent case unit 19 and covers the reagent case unit 19.

The holding unit 21 pivotally holds the reagent bottles 6 housed in the reagent case unit 19. The holding unit 21 is spaced apart from the reagent case 190 and the reagent cover 20. The holding unit 21 comprises a first tray 30 and a second tray 32. The first tray 30 pivotally holds first racks 31 which hold the reagent bottles 6. The second tray 32 pivotally holds second racks 33 which hold the reagent bottles 6. The first and second trays 30 and 32 are lower than the edge of the reagent case 190. The reagent bottles 6 held by the first and second trays 30 and 32 are lower than the edge of the reagent case 190.

The cooling unit 22 keeps the reagent bottles 6 at a predetermined temperature. The cooling unit 22 is mounted on the outer bottom surface of the reagent case 190 to cool the reagent case 190. The cooling unit 22 comprises, for example, a Peltier device, a temperature sensor which detects a temperature at a predetermined position in the reagent case 190, and a control circuit which controls the Peltier device on the basis of a temperature detection signal from the temperature sensor.

The thermal insulating unit 23 thermally insulates the reagent case unit 19. The thermal insulating unit 23 comprises a thermal insulating member which covers the outer surface of the reagent case 190 of the reagent case unit 19.

The circulating unit 24 is placed in the reagent case unit 19. The circulating unit 19 circulates, in the reagent case unit 19 closed by the reagent cover 20, air contained in spaces such as a first space 25, second spaces 26 and 27, and a third space 28. The first space 25 is formed between the bottom surface of the reagent case unit 19 and the bottom portion of the holding unit 21. The second spaces 26 and 27 are formed between the adjacent reagent bottles 6. The third space 28 is formed in the central portion of the holding unit 21. The circulating unit 24 comprises, for example, a fan with excellent waterproofness. The circulating unit 24 is placed in the third space 28 or the first space 25 near the center of the holding unit 21.

Note that the second reagent storage 2 differs from the first reagent storage 1 in the position at which the analytical unit 18 is placed and in that the reagent bottles 7 are cooled. Since the second reagent storage 2 has the same arrangement as that of the first reagent storage 1, and the reagent bottle 7 has the same shape as that of the reagent bottle 6, a description of them will be omitted.

Figure 5:
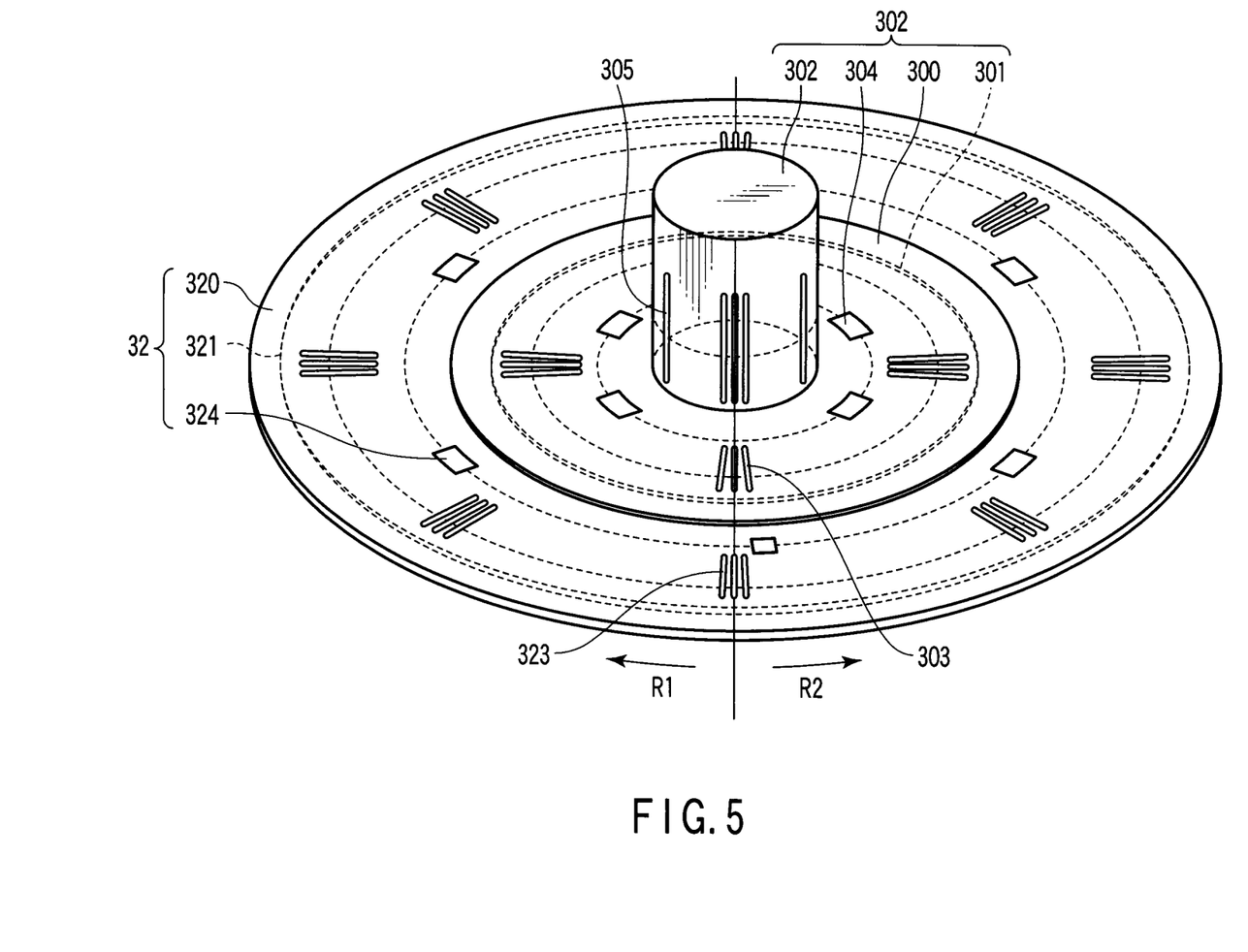
FIG. 5 is a perspective view showing the arrangement of the first and second trays in FIG. 2.
Figure 6:
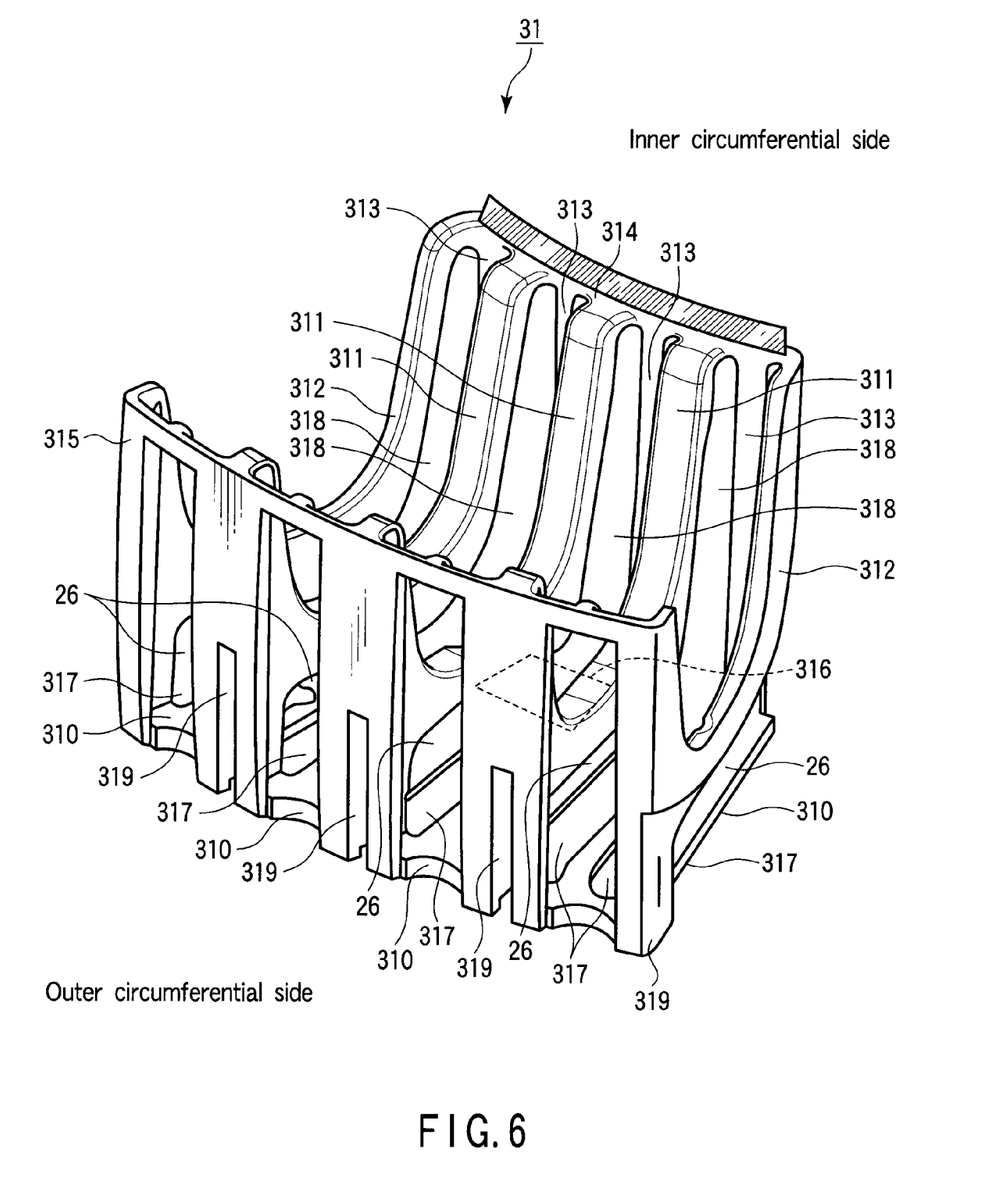
FIG. 6 is a perspective view showing the arrangement of the first rack in FIG. 2.
Figure 7:
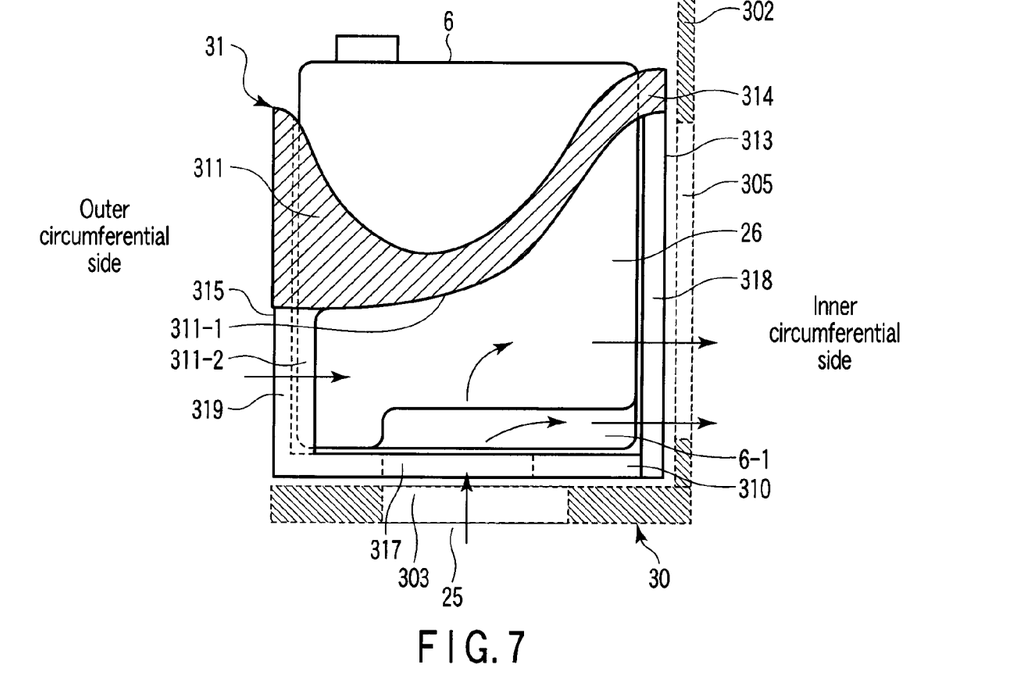
FIG. 7 is a sectional view of the first rack in the first reagent storage taken along line B-B' of FIG. 3.
Figure 8:
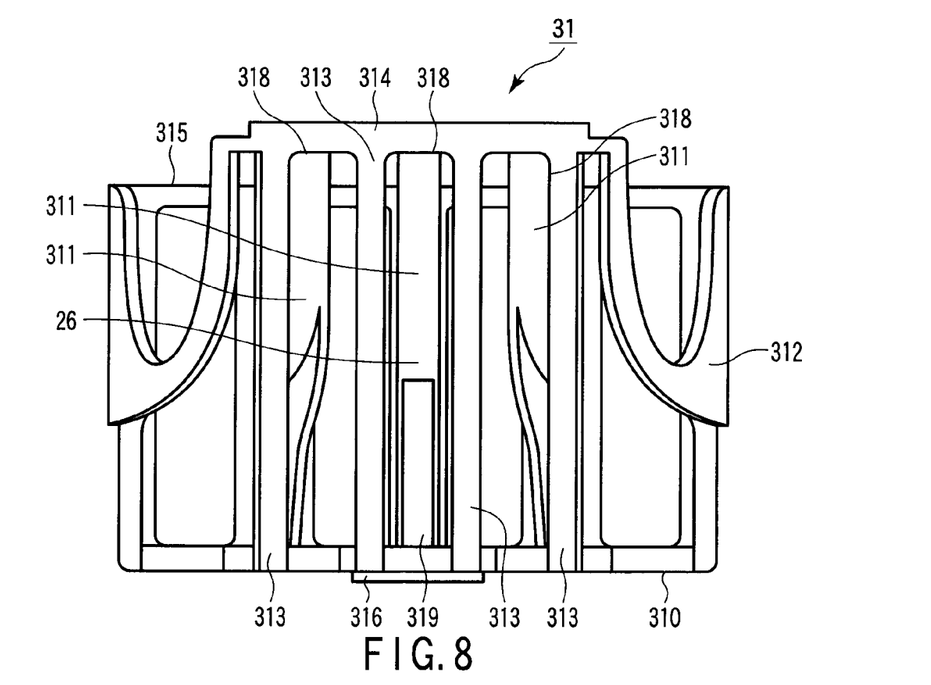
FIG. 8 is a view showing the first rack in FIG. 2 when viewed from the inner circumferential side.
Figure 9:
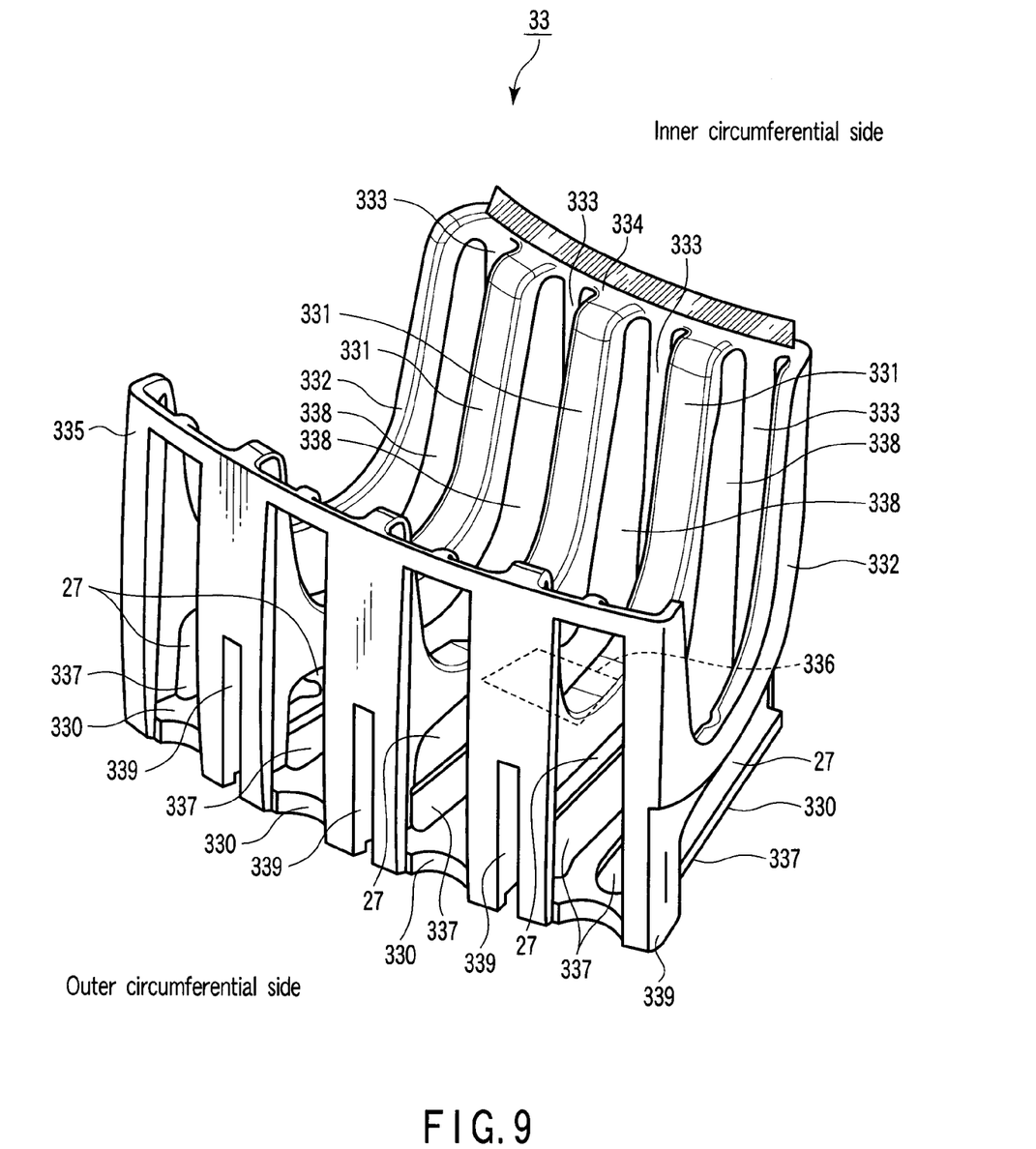
FIG. 9 is a perspective view showing the arrangement of the second rack in FIG. 2.

The arrangements of the first tray 30, second tray 32, first racks 31, and second racks 33 will be described in detail next with reference to FIGS. 3 to 9. FIG. 5 is a perspective view showing the arrangements of the first tray 30 and second tray 32. FIG. 6 is a perspective view showing the arrangement of the first rack 31. FIG. 7 is a sectional view of the first rack 31 in the first reagent storage 1 taken along line B-B' of FIG. 3. FIG. 8 is a view showing the first rack 31 when viewed from the inner circumferential side. FIG. 9 is a perspective view showing the arrangement of the second rack 33.

As shown in FIG. 5, the first tray 30 comprises a first disk 300, a first guide 301, a tray cover 302, and first holding members 304. The first disk 300 holds the first racks 31 from below. The first disk 300 has a doughnut shape and a circular opening portion in the central portion. The first guide 301 has an annular shape and is fixed to the lower surface of the first disk 300. The tray cover 302 covers the circular opening in the central portion of the first disk 300 from above. The first holding member 304 comprises a magnet, magnetic member, or the like for holding the first rack 31.

The first disk 300 has many first openings 303 to allow air to circulate between the first space 25 and the bottom portions of the first racks 31. The many first openings 303 are provided on the circumference of the first disk 300. The first disk 300 detachably holds the first racks 31 with the first holding members 304.

The upper surface of the first guide 301 is fixed to the lower surface of the first disk 300. The rollers 192 arranged on the first circumference of the bottom surface of the reagent case 190 are mounted on the lower surface of the first guide 301. An inner side surface of the first guide 301 is engaged with a pinion gear attached to the rotating shaft of a first motor (drive unit 41) M1. As the first motor M1 rotates, the first disk 300 pivots in the direction indicated by an arrow R1 or R2.

The tray cover 302 is placed near the first rack 31. The tray cover 302 comprises a wall surface member having a tubular shape with an upper opening being closed. The tray cover 302 forms the third space 28. A side surface of the tray cover 302 has many fourth openings 305 to allow air to circulate between side portions of the first racks 31 and the third space.

The second tray 32 is placed near the outer surface of the first disk 300 of the first tray 30. The second tray 32 comprises a second disk 320, a second guide 321, and first holding members 324. The second disk 320 has a doughnut shape and holds the second racks 33. The second guide 321 has an annular shape and is fixed to the lower surface of the second disk 320. The first holding member 324 comprises a magnet, magnetic member, or the like for holding the second rack 33.

The second disk 320 has many first openings 323 to allow air to circulate between the first space 25 and the bottom portions of the second racks 33. The first openings 323 are provided on the circumference of the second disk 320. The second disk 320 detachably holds the second racks 33 with the first holding members 324.

The upper surface of the second guide 321 is fixed to the lower surface of the second disk 320. The lower surface of the second guide 321 is engaged with the rollers 192 arranged on the second circumference of the bottom surface of the reagent case 190. An inner side surface of the second guide 321 is engaged with, for example, a pinion gear attached to the rotating shaft of a second motor (drive unit 41) M2. As the second motor M2 rotates, the second disk 320 pivots in the direction indicated by an arrow R1 or R2.

FIG. 6 is a perspective view showing the arrangement of the first rack 31. The first rack 31 comprises base plates 310, partition plates 311, end side plates 312, inner holding plates 313, an inner plate 314, an outer plate 315, and a second holding member 316. The N base plates 310 respectively hold the bottom portions of the N reagent bottles 6. The partition plates 311 hold the side portions of the reagent bottles 6 such that side portions are spaced apart from each other by a predetermined interval. The (N−1) partition plates 311 are respectively arranged at (N−1) portions of the first racks 31. The end side plates 312 are arranged at the two end portions of the first racks 31 in the pivoting direction. The inner holding plates 313 hold the side portions (inner portions) of the respective reagent bottles 6 which are located on the tray cover 302 side (inner circumferential side).

The inner plate 314 couples the upper end portions of the partition plates 311, the end side plates 312, and the inner holding plates 313. The outer plate 315 holds the side portions (outer portions) of the respective reagent bottles 6 which are located on the outer circumferential side which is the second tray 32 side. The second holding member 316 comprises a magnet, magnetic member, or the like which is engaged with the first holding member 304 of the first tray 30 fixed to the lower surface of the base plate 310.

Second openings 317 are provided in the base plate 310 at positions immediately below the reagent bottles 6 and between the adjacent reagent bottles 6 so as to allow air to circulate between the first space 25 and the second spaces 26 through the first openings 303 of the first tray 30.

The partition plates 311 are arranged at intervals. A lower end portion 311-1 of the partition plate 311 on the outer circumferential side is integrated with the base plate 310. A side end portion of the partition plate 311 on the outer circumferential side is integrated with the outer plate 315. A portion 311-2 of the partition plate 311 which is located near the side end portion on the outer circumferential side is hollowed. The upper end portion of the partition plate 311 on the inner circumferential side is integrated with the inner plate 314.

As shown in FIG. 7, the second space 26 is formed by the lower surface of the partition plate 311, side surfaces of the adjacent reagent bottles 6, and a depressed surface 6-1 formed by a depression extending inward from a portion near the outer portion of the bottom portion of the reagent bottle 6 to its inner portion. The first space 25 is connected to the second spaces 26 through the first openings 303 and the second openings 317.

The end side plate 312 is spaced apart from the partition plate 311. The lower end portion of the end side plate 312 on the outer circumferential side is integrated with the base plate 310. The side end portions of the end side plates 312 on the outer circumferential side are integrated with the outer plate 315. A combination of the adjacent end side plates 312 has almost the same structure as that of the partition plate 311.

The inner holding plates 313 are arranged between the partition plates 311 and the end side plates 312 and between the partition plates 311 so as to be spaced apart from the partition plates 311 and the end side plates 312. The inner holding plates 313 are arranged near a side portion of the tray cover 302. The upper end portions of the inner holding plates 313 are integrated with the inner plate 314. The lower end portions of the inner holding plates 313 are integrated with the base plates 310.

With this structure, as shown in FIG. 8, third openings 318 are formed by the adjacent inner holding plates 313 and the inner plate 314. The second space 26 is connected to the third space 28 through the third openings 318 and the fourth openings 305.

The outer surface of the inner plate 314 has almost the same curvature as that of a circular opening of the first disk 300. The inner plate 314 connects the upper end portions of the partition plates 311, end side plates 312, and inner holding plates 313.

The outer surface of the outer plate 315 has almost the same curvature as that of the outer circumference of the first disk 300. The outer plate 315 has fifth openings 319 so as to allow air to circulate between the outer circumferential sides of the first racks 31 and the second spaces 26 through hollow portions at the side end portions of the partition plates 311. The outer plate 315 also has an opening at a position corresponding to the outer portion of the reagent bottle 6 so as to allow the reader 1c to read the bar code label attached to the outer surface of the reagent bottle 6.

FIG. 9 is a perspective view showing the arrangement of the second rack 33. The second rack 33 is located near the outer circumference of the first rack 31. The second rack 33 differs from the first rack 31 in that the curvatures on the outer circumferential side and the inner circumferential side are almost the same as those of the outer circumference and inner circumference of the second disk 320 which are smaller than those of the outer plate 315 and inner plate 314 of the first rack 31, and the respective opening portions differ in size because of the differences in the curvatures on the outer circumferential side and the inner circumferential side. Note that the components of the second rack 33 which have the same structures and functions as those of the first rack 31 will be called by the same terms and denoted by different reference numbers. These components will be briefly described below.

The second rack 33 comprises base plates 330, partition plates 331, end side plates 332, inner holding plates 333, an inner plate 334, an outer plate 335, and second holding members 336. The base plates 330 respectively hold the bottom portions of the respective reagent bottles 6. The partition plates 331 hold the reagent bottles 6 such that the adjacent reagent bottles 6 are spaced apart from each other by a predetermined interval. The end side plates 332 hold the outer side portions of the reagent bottles 6 at the end portions in the pivoting direction of the second rack 33. The inner holding plates 333 hold the side portions of the respective reagent bottles 6. The inner plate 334 couples the upper end portions of the partition plates 331, the end side plates 332, and the inner holding plates 333. The outer plate 335 holds the outer portions of the reagent bottles 6. The second holding member 336 comprises a magnet, magnetic member, or the like which is engaged with the first holding member 324 of the second tray 32.

Second openings 337 are provided in the base plate 330 at positions immediately below the reagent bottles 6 and between the adjacent reagent bottles 6 so as to allow air to circulate between the first space 25 and the insides of the second racks 33 through the first openings 323 of the second tray 32.

A second space 27 is formed by a lower end surface 311-1 of the partition plate 331, side surfaces of the adjacent reagent bottles 6, and the depressed surface 6-1 of the reagent bottle 6. The first space 25 is connected to the second spaces 27 through the first openings 323 and the second openings 337. Note that the depressed surface 6-1 comprises a depression extending inward from a portion near the outer portion of the bottom portion of the reagent bottle 6 to its inner portion.

The outer surface of the inner plate 334 has almost the same curvature as that of the inner circumference of the second disk 320. The outer surface of the outer plate 335 has almost the same curvature as that of the outer circumference of the second disk 320. A third opening 338 is formed by the adjacent inner holding plates 333 and the inner plate 334.

If it is not necessary to house many reagent bottles 6, the first reagent storage can comprise a reagent case and a reagent cover which are reduced to sizes enough to house the first tray 30 and the first racks 31 by omitting the second tray 32 and the second racks 33. This can reduce the size of the apparatus.

If it is not necessary to use many reagent bottles 6 and 7, the second reagent dispensing probe 15 and the second reagent dispensing arm 9 may be arranged at positions where the reagent bottles 6 and 7 can be housed in the first reagent storage 1 and the second reagent can be drawn from the reagent bottle 7 in the first reagent storage 1 and discharged to the reaction vessel 3. This can reduce the size of the apparatus.

If it is necessary to house many reagent bottles 6, the first reagent storage can comprise a third tray and third racks arranged the second tray 32 and the second racks 33, in addition to a reagent case and a reagent cover which are increased in size enough to house the third tray and the third racks.

The operation of storing and cooling the first reagent stored in each reagent bottle 6 in the first reagent storage 1 of the automatic analyzer 100 will be described below with reference to FIGS. 1 to 9.

When the automatic analyzer 100 is powered on, the cooling unit 22 and circulating unit 24 of the first reagent storage 1 operate. The cooling unit 22 cools the air contained in the first and fourth spaces 25 and 29 in the reagent case 190 and reagent cover 20 by cooling the reagent case 190. The circulating unit 24 aspirates the air contained in the third space 28 in the tray cover 302 and discharges the air into the first and fourth spaces 25 and 28. This makes the air cooled in the first and fourth spaces 25 and 29 flow into the second spaces 26 and 27 formed in the first and second racks 31 and 33. The air flowed into the second spaces 26 and 27 flows into the third space 28 through the fourth openings 305. The air flowed into the third space 28 is aspirated into the circulating unit 24 again. In this manner, the circulating unit 24 directly blows air against the bottom surface of the reagent case 190. This increases the thermal conductivities of the reagent case 190 and air in the first reagent storage 1 as compared with the case in which the air cooled in the first and fourth spaces 25 and 29 is blown against the tray cover 302.

At the second racks 33 and the reagent bottles 6 held on the second racks 33, the air cooled in the first space 25 flows into the second spaces 27 through the first openings 323 of the second tray 32 and the second openings 337 of the second racks 33. The air cooled in the fourth space 29 is prevented by the projection 191 from flowing to above the reagent bottles 6, and flows into the second space 27 through fifth openings 339 of the second tray 32.

The partition plates 331 and end side plates 332 of the second racks 33 prevent the air flowing into the second spaces 27 from flowing to above the reagent bottles 6. The air then passes between the side surfaces of the adjacent reagent bottles 6 and the depressed surfaces 6-1 which form the second spaces 27. At this time, the air cools the first reagent in each reagent bottle 6. The passed air flows from the third openings 338 formed in the second racks 33.

In this manner, since the air cooled in the first and fourth spaces 25 and 29 can be made to flow to the side portions and bottom portions of the respective reagent bottles 6 forming the second spaces 27, the cooled air can be blown against a wide area of each reagent bottle 6. This makes it possible to efficiently keep the first reagent cool in each reagent bottle 6.

The projection 191 prevents the air cooled in the fourth space 29 from flowing above the reagent bottles 6. In addition, the partition plates 331 and end side plates 332 of the second racks 33 prevent the air flowing into the second spaces 27 from flowing above the reagent bottles 6. This can restrict the flow of air flowing into the second spaces 27 and prevent the first reagent in each reagent bottle 6 from evaporating. Restricting the flow of air to above the reagent bottles 6 can prevent contamination of the first reagent in another reagent bottle 6 which is caused when the vapor of the first reagent in a given reagent bottle mixes with the first reagent in another reagent bottle 6.

At the first racks 31 and the reagent bottles 6 held on the first racks 31, the air cooled in the first space 25 flows into the second spaces 26 through the first openings 303 formed in the first tray 30 and the second openings 317 formed in the first racks 31. The air flowing from the third openings 338 formed in the second racks 33 flows to the second spaces 26 through the fifth openings 319 formed in the first racks 31.

The partition plates 311 and the end side plates 312 of the first racks 31 prevent the air flowing into the second spaces 26 from flowing to above the reagent bottles 6. The air then passes between the side surfaces of the adjacent reagent bottles 6 and the depressed surfaces 6-1 which form the second spaces 26. At this time, the air cools the first reagent in each reagent bottle 6. The passed air flows from the third openings 318 formed in the first racks 31.

In this manner, since the air cooled in the first space 25 can be made to flow to the side portions and bottom portions of the reagent bottles 6 forming the second spaces 26, the cooled air can be blown against a wide area of each reagent bottle 6. This makes it possible to efficiently keep the first reagent cool in each reagent bottle 6.

In addition, the partition plates 311 and end side plates 312 of the first racks 31 can prevent air flowing into the second spaces 27 from flowing to above the reagent bottles 6. This can suppress evaporation of the first reagent from each reagent bottle 6.

In the tray cover 302, air flowing from the third openings 318 formed in the first racks 31 flows into the third space 28 through the fourth openings 305 formed in the tray cover 302 located near the first racks 31. At this time, since the upper portion of the tray cover 302 is covered, the flow of air from the space above the reagent bottles 6 can be prevented.

In this manner, since the tray cover 302 can prevent air from flowing from the space above the reagent bottles 6, the evaporation of the first reagent from each reagent bottle 6 can be suppressed.

Note that the reagent bottles 7 in the second reagent storage 2 are kept cool in the same manner as the reagent bottles 6 in the first reagent storage 1, thereby obtaining the same effects as described above.

According to the above embodiment, air cooled in the first space 25 can be made to flow to the side portions and bottom portions of the respective reagent bottles 6 held in the first racks 31 which form the second spaces 26. In addition, the air cooled in the first space 25 and the fourth space 29 can be made to flow to the side portions and bottom portions of the respective reagent bottles 6 held in the second racks 33 which form the second spaces 27. This makes it possible to blow cooled air against a wide area of each reagent bottle 6, thereby efficiently storing and cooling the first reagent in each reagent bottle 6.

In addition, the partition plates 311 and end side plates 312 of the first racks 31 and the partition plates 331 and end side plates 332 of the second racks 33 can prevent air flowing into the second spaces 26 and 27 from flowing out to above the reagent bottles 6. In addition, the projection 191 can prevent the air cooled in the fourth space 29 from flowing to above the reagent bottles 6. Furthermore, the tray cover 302 can prevent air from being flowed from the space above the reagent bottles 6. This can suppress evaporation of the first reagent from each reagent bottle 6 and hence prevent a deterioration in analytical data.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A reagent storage for an automatic analyzer, the storage comprising:
    a holding unit which pivotally holds a plurality of reagent bottles which store reagents;
    a case which houses the holding unit and has an edge higher than at least the housed holding unit;
    a cover for closing the case;
    a cooling unit which is mounted on a first portion of the case and cools air in the case, wherein the first portion of the case is a continuous wall on an outer surface of the case which prevents air from entering into the case from the cooling unit; and
    a circulating unit which is mounted on the holding unit and which circulates the cooled air in the case closed by the cover, the circulating unit moving air towards the cooled outer surface.

2. The storage according to claim 1, which further comprises a wall surface member having a bottom surface and a side surface in which a first opening is formed, and in which the wall surface member is mounted on the holding unit so as to cover the circulating unit.

3. The storage according to claim 2, wherein at least a portion of the first opening is formed at or below a substantially central portion of the held reagent bottle in a height direction.

4. The storage according to claim 2, wherein
    the cooling unit cools air contained in a first space between an inner bottom surface of the case and a bottom surface of the holding unit, and
    the circulating unit makes the cooled air flow into a second space formed between the adjacent reagent bottles by drawing air contained in a third space in the wall surface member and discharging the drawn air into the first space.

5. The storage according to claim 4, wherein the circulating unit is placed in one of the first space and the third space.

6. The storage according to claim 4, wherein
    the holding unit has a rack which holds portions of a side surface and bottom surface of the reagent bottle placed on an outer circumference of the third space and a tray which holds the rack from below, and
    the first space is connected to the second space through a third opening provided in the tray and a fourth opening provided in a bottom portion of the rack.

7. The storage according to claim 6, wherein
    the rack has a fifth opening provided at a position near the wall surface member, and
    the second space is connected to the third space through the first opening and the fifth opening.

8. The storage according to claim 6, wherein
    the rack comprises a partition plate which separates the adjacent reagent bottles by a predetermined interval, and
    the second space is formed by the adjacent reagent bottles and a lower surface of the partition plate.

9. The storage according to claim 6, wherein
    the holding unit comprises a first magnet for detachably holding the rack on the tray and a second magnet or magnetic member which is engaged with the first magnet, and
    the first magnet is fixed on an upper surface of the tray, and the second magnet or magnetic member is fixed on a lower surface of a bottom portion of the rack.

10. The storage according to claim 6, wherein
the rack comprises a first rack which holds the reagent bottle arranged on the circumference and a second rack which is arranged near an outer circumference of the first rack and holds the reagent bottle, and
the tray comprises a first tray which pivotally holds the first rack and a second tray which pivotally holds the second rack.

11. The storage according to claim 1, wherein
the holding unit has a bottom portion which holds the reagent bottle, and
the bottom portion has a second opening for circulating the cooled air.

12. The storage according to claim 1, wherein a projection which prevents the cooled air from flowing to above the reagent bottle is formed on an inner side surface of the case.

13. A reagent storage for an automatic analyzer, the storage comprising:
a case which houses a reagent bottle storing a reagent;
a cover for closing the case;
a holding unit which is arranged in the case closed by the cover so as to be spaced apart from the case and the cover and hold the reagent bottles which are spaced apart from each other by a predetermined interval; and
a circulating unit connecting a first space between an inner bottom surface of the case and a bottom portion of the holding unit to a second space formed between adjacent reagent bottles held by the holding unit, and connecting the second space to a third space formed near a center of the holding unit, and which aspirates air from the third space by moving the air into the first space, and discharges air cooled in the first space into the second space.

14. The storage according to claim 13, wherein the circulating unit is placed in one of the first space and the third space.

15. The storage according to claim 13, wherein an inner side surface of the case is provided with a projection which prevents air contained in a fourth space between the side surface and the holding unit from flowing to above the reagent bottle.

16. The storage according to claim 13, wherein
the holding unit comprises a rack which holds portions of a side surface and the bottom surface of the reagent bottle arranged on an outer circumference of the third space and a tray which movably holds the rack from below, and
the first space is connected to the second space through a first opening provided in the tray and a second opening provided in a bottom portion of the rack.

17. The storage according to claim 16, wherein
the tray comprises a disk which holds the rack and has a third opening in a central portion and a tray cover which forms the third space by covering the third opening from above and is arranged near the rack, and
the second space is connected to the third space through the third opening and a fourth opening provided in the tray cover.

18. The storage according to claim 16, wherein
the rack comprises a partition plate which separates the adjacent reagent bottles by a predetermined interval, and the second space is formed by the adjacent reagent bottles and a lower surface of the partition plate.

19. The storage according to claim 16, wherein the rack has a fifth opening which connects a fourth space between an inner side surface of the reagent case and the holding unit to the second space.

20. The storage according to claim 16, wherein
the holding unit comprises a first magnet for detachably holding the rack on the tray and a second magnet or magnetic member which is engaged with the first magnet, and
the first magnet is fixed on an upper surface of the tray and the second magnet or magnetic member is fixed on a lower surface of a bottom portion of the rack.

21. The storage according to claim 16, wherein
the rack comprises a first rack which holds the reagent bottle arranged on a circumference and a second rack which holds the reagent bottle arranged near an outer circumference of the first rack, and
the tray comprises a first tray which pivotally holds the first rack and a second tray which pivotally holds the second rack.

22. The storage according to claim 13, wherein the circulating unit includes at least one revolving blade.

23. An automatic analyzer comprising:
a reagent storage which stores a reagent; and
a measurement unit which measures a mixture of the reagent and a sample, the reagent storage comprising:
a holding unit which pivotally holds a plurality of reagent bottles which store reagents;
a case which houses the holding unit and has an edge higher than at least the housed holding unit;
a cover for closing the case;
a cooling unit which is mounted on a first portion of the case and cools air in the case, wherein the first portion of the case is a continuous wall on an outer surface of the case which prevents air from entering into the case from the cooling unit; and
a circulating unit which is mounted on the holding unit and which circulates the cooled air in the case closed by the cover, the circulating unit moving air towards the cooled outer surface.

24. An automatic analyzer which dispenses a sample and a reagent and measures a mixture thereof, the apparatus comprising a reagent storage having a case which houses a reagent bottle storing the reagent and a cover which covers the case, and the reagent storage comprising:
a holding unit which is arranged in the case closed by the cover so as to be spaced apart from the case and the cover and hold the reagent bottles which are spaced apart from each other by a predetermined interval;
a cooling unit which cools the case; and
a circulating unit connecting a first space between an inner bottom surface of the case and a bottom portion of the holding portion to a second space formed between adjacent reagent bottles held by the holding unit, and connecting the second space to a third space formed near a center of the holding unit, and which aspirates air from the third space by moving the air into the first space, and discharges air cooled in the first space into the second space.

* * * * *